(12) United States Patent
Yin et al.

(10) Patent No.: US 10,258,574 B2
(45) Date of Patent: Apr. 16, 2019

(54) METHOD OF PREPARING ITRACONAZOLE PREPARATION

(71) Applicants: CHANGZHOU PHARMACEUTICAL FACTORY CO., LTD., Changzhou (CN); CRYSTEC LTD., Bradford (GB)

(72) Inventors: Xuezhi Yin, Changzhou (CN); Linda Sharon Daintree, Bradford (GB); Sheng Ding, Changzhou (CN); Daniel Mark Ledger, Bradford (GB); Bing Wang, Changzhou (CN); Wenwen Zhao, Changzhou (CN); Wei Wu, Changzhou (CN); Jiansheng Han, Changzhou (CN)

(73) Assignees: CHANGZHOU PHARMACEUTICAL FACTORY CO., LTD., Changzhou (CN); CRYSTEC LTD., Bradford (GB)

( * ) Notice: Subject to any disclaimer, the term of this patent is extended or adjusted under 35 U.S.C. 154(b) by 119 days.

(21) Appl. No.: 15/555,081

(22) PCT Filed: Sep. 8, 2015

(86) PCT No.: PCT/CN2015/089129
§ 371 (c)(1),
(2) Date: Sep. 1, 2017

(87) PCT Pub. No.: WO2016/123973
PCT Pub. Date: Aug. 11, 2016

(65) Prior Publication Data
US 2018/0263912 A1 Sep. 20, 2018

(30) Foreign Application Priority Data
Feb. 3, 2015 (CN) .......................... 2015 1 0057090

(51) Int. Cl.
*A61K 9/16* (2006.01)
*A61K 31/496* (2006.01)
(Continued)

(52) U.S. Cl.
CPC .......... *A61K 9/1694* (2013.01); *A61K 9/4858* (2013.01); *A61K 9/4866* (2013.01);
(Continued)

(58) Field of Classification Search
CPC .. A61K 9/1694; A61K 9/4858; A61K 9/4866; A61K 31/496; A61K 47/10; A61K 47/38
See application file for complete search history.

(56) References Cited

U.S. PATENT DOCUMENTS

2006/0062848 A1* 3/2006 German ............... A61K 9/1635
424/464

FOREIGN PATENT DOCUMENTS

CN 1449744 A * 10/2003 ........... A61K 9/5078

OTHER PUBLICATIONS

Joo Won Park et al., Arch. Pharm. Res. 2013, 36, 1369-1376.*
Sathigari et al., J. Pharm. Sci., 2011, 100, 2952-2965.*

* cited by examiner

Primary Examiner — Vu A Nguyen
(74) Attorney, Agent, or Firm — Gokalp Bayramoglu

(57) ABSTRACT

A method for preparing an itraconazole formulation including: dissolving a mixture of itraconazole and L-ascorbic acid with a mixed solvent of dichloromethane and methanol, adding a hydroxypropyl methylcellulose and a pluronic F-127 and then dichloromethane into the mixed solvent to obtain a raw material solution; feeding a carbon dioxide into a crystallization autoclave in a supercritical fluid crystallization equipment system through a pressure regulating valve; spraying the solution into the crystallization autoclave
(Continued)

via a spray nozzle, separating out composite particles from the solution and collecting the composite particles at a bottom of the crystallization autoclave, and encapsulating the composite particles to obtain a itraconazole formulation with decreased particle size and increased bioavailability.

6 Claims, 2 Drawing Sheets

(51) Int. Cl.
    *A61K 9/48*         (2006.01)
    *A61K 47/10*       (2017.01)
    *A61K 47/38*       (2006.01)

(52) U.S. Cl.
    CPC ............ *A61K 31/496* (2013.01); *A61K 47/10* (2013.01); *A61K 47/38* (2013.01)

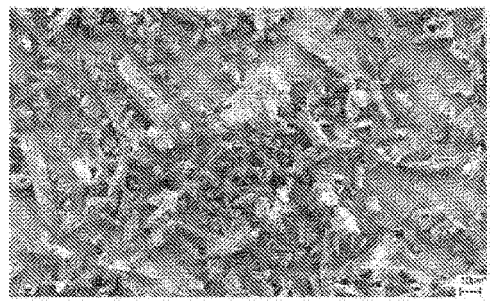 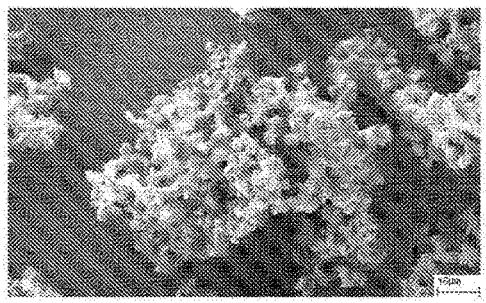
FIG.2c　　　　　　　　　FIG.2d
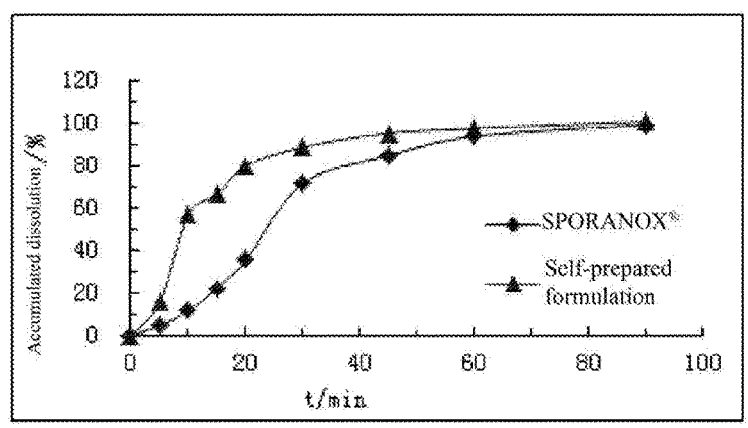
FIG.3
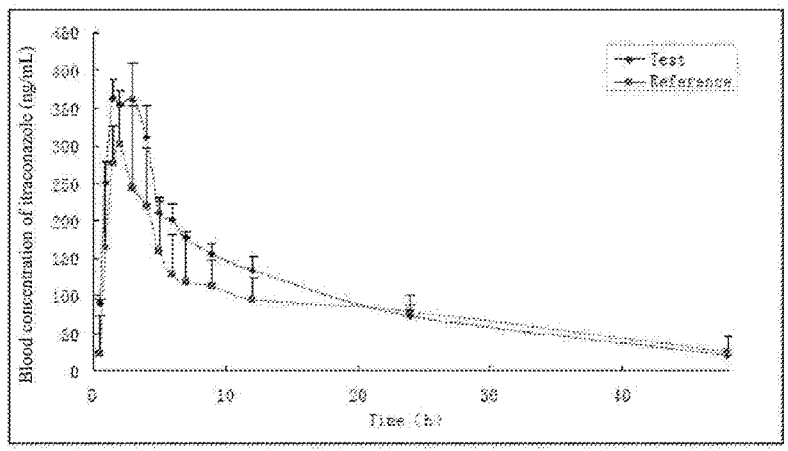
FIG.4

METHOD OF PREPARING ITRACONAZOLE PREPARATION

CROSS REFERENCE TO RELATED APPLICATIONS

This application is the national phase entry of International Application No. PCT/CN2015/089129, filed on Sep. 8, 2015, which is based upon and claims priority to Chinese Patent Application No. CN 201510057090.2, filed on Feb. 3, 2015, the entire contents of which are incorporated herein by reference.

TECHNICAL FIELD

The present invention relates to a field of pharmaceutical preparation, and more particularly to a method for preparing an efficient itraconazole formulation.

BACKGROUND

Itraconazole is a triazole antifungal agent, which has been marketed since 1988. It has broad-spectrum activity against both fungi and bacteria and some protozoa, and is effective against *Candida, Aspergillus, Cryptococcus, Histoplasma,* and *Blastomyces*. Itraconazole has strong lipophilicity and is very sparingly soluble in water with a saturated solubility of <1 ng/mL in an aqueous solution at a neutral pH and a saturated solubility of 6 μg/mL in a hydrochloric acid solution at pH=1. Itraconazole is a typical class II drug under the Biopharmaceutics Classification System, and its oral bioavailability depends on the dissolution rate of the drug in the gastrointestinal tract. Because itraconazole is poorly soluble in water, it has a small dissolution rate in the gastrointestinal tract and low oral bioavailability; and also, it is difficult to make an itraconazole injection with a high drug level, resulting in a large dosage amount.

SPORANOX (with itraconazole as a main ingredient) injection, oral liquid and capsule are currently commercially available itraconazole formulations. The solubility of the injection and oral liquid is increased by complexing itraconazole with 2-hydroxypropyl-β-cyclodextrin, but 2-hydroxypropyl-β-cyclodextrin is eliminated primarily by the kidney, so that the elimination time may be prolonged substantially for a patient with serious renal dysfunction, possibly leading to cumulative poisoning. In addition, it has been reported that although the clinical relevance is yet unclear, 2-hydroxypropyl-β-cyclodextrin is found to cause pancreatic cancer in a rat carcinogenicity study of 2-hydroxypropyl-β-cyclodextrin. A study for the SPORANOX capsule has shown that its oral bioavailability highly varies between individuals, and is significantly affected by the gastric acid secretion and diet of patients. Thus, seeking an efficient, low toxic, highly bioavailable, and stable formulation has become a research hotspot in development of itraconazole formulations.

In order to overcome the poor solubility and low bioavailability of itraconazole and the problems of commercial itraconazole formulations, in terms of the formulation, research institutions at home and abroad have made a series of attempts using modern administration techniques, so as to prepare itraconazole into an intravenous emulsion, a self-emulsifying agent and a polymeric micelle, achieving the solubilization effect. However, some problems still exist in the dosage forms. For example, the self-emulsifying agent contains an amount of concentrated hydrochloric acid in the formulation and will lead to damage to the digestive tract for direct administration, and thus further need to be encapsulated in a solid state before oral administration. For the polymeric micelle, polymers used and the safety of respective degraded products in the body have not been reported in literature.

Decreasing the particle size may be used to improve the solubility of a non-water-soluble drug. Supercritical fluid crystallization technique is a new approach for preparing a micro drug, the principle of which is that: a drug solution is mixed with a supercritical fluid such as carbon dioxide under a supercritical state and is sprayed from a spray nozzle so as to form micron-sized particles within several tens of microseconds, where the particle size and crystal form of the drug can be controlled by adjusting the parameters such as pressure, temperature, flow, concentration. The supercritical fluid crystallization technique also enables the drug and polymeric adjuvants to form micron-sized composite particles, so as to ensure the solubility and thus efficacy of the drug, and the composite particles have good crystal stability.

SUMMARY

The objective of the present invention is to prepare an efficient itraconazole formulation by using the supercritical fluid crystallization technique, thereby increasing the bioavailability and efficacy of the drug, and avoiding the use of a surfactant to reduce side effects of the drug.

A schematic diagram of a supercritical fluid crystallization equipment is show in FIG. 1.

The present invention provides a method for preparing an itraconazole formulation, comprising the following four steps:

1) preparing a mixed solution: adding a mixed solvent of methanol and dichloromethane into a mixture of itraconazole and L-ascorbic acid, dissolving the mixture of itraconazole and L-ascorbic acid thereof, adding a hydroxypropyl methylcellulose and a pluronic F-127 and then a dichloromethane into the mixed solvent, dissolving;

2) feeding a carbon dioxide: feeding the carbon dioxide in a steel tank into a crystallization autoclave in a supercritical fluid crystallization equipment system through a pressure regulating valve;

3) separating out a composite particle (comprising an active drug and a polymer material): spraying the solution obtained in the step (1) into the crystallization autoclave via a spray nozzle of the supercritical fluid crystallization equipment system, separating out the composite particles out from the solution and collecting the composite particles at a bottom of the crystallization autoclave; and 4) encapsulating the composite particles obtained (formulation specifications: 50 mg/capsule and/or 100 mg/capsule);

wherein, the weight percentage of the itraconazole in a content of a capsule is 30%-55%;

a volume ratio of the methanol to the dichloromethane is 1:1-1:9;

a flow rate of the carbon dioxide is 10-50 ml/min;

a pressure is 50-130 Bar; and a flow rate of the solution is 0.1-3 ml/min.

The content of the itraconazole capsule prepared according to the method described above is determined by X-ray powder diffraction and SEM. The results are shown in FIG. 2, where FIG. 2*a* and FIG. 2*c* are the X-ray powder diffraction and SEM spectra of drug substance of itraconazole, and FIG. 2*b* and FIG. 2*d* are the X-ray powder diffraction and SEM spectra of the itraconazole composite particles in the efficient formulation. As seen in FIG. 2, the itraconazole composite particles in the efficient formulation have a smaller and more uniform particle size, meaning that the self-prepared formulation may provide better effects in the body.

An in vitro dissolution test is carried out for the self-prepared capsule (self-prepared formulation) in accordance with Method 2 (paddle method) in Appendix X of the Chinese Pharmacopoeia 2010 edition, with a rotation speed of 75 r/min, using the same dose of a commercially available itraconazole capsule from an original plant (trade name: SPORANOX, Xian Janssen Pharmaceutical Ltd.) as a control drug. The dissolution profiles are measured in a pH 1.0 aqueous solution and the test results are shown in FIG. 3. As seen in the figure, our efficient formulation exhibits a faster dissolution rate compared to the commercially available SPORANOX capsule.

An in vivo test in a dog is carried out with the prepared efficient itraconazole formulation (Test), using a commercially available SPORANOX capsule as a control drug (Reference). The determination is performed with liquid chromatography-mass spectrometry. Drug-time curves are shown in FIG. 4, and in vivo pharmacokinetic data is shown in the table below. As seen in the figure and table, compared to the commercially available SPORANOX capsule, the self-prepared formulation exhibits a faster absorption rate and a greater maximum blood concentration Cmax (Cmax of 423±61 ng/mL for the self-prepared formulation and Cmax of 305±11 ng/mL for the commercially available SPORANOX). Also, the self-prepared formulation exhibits a bioavailability of 120% with respect to SPORANOX, that is, the self-prepared formulation has a better bioavailability.

Pharmacokinetic data of the self-prepared formulations:

| NO | T1/2 H | CMAX ng/ml | TMAX H | AUC ng/ml * h |
|---|---|---|---|---|
| 1 | 15.27 | 366 | 2 | 4139 |
| 2 | 15.28 | 417 | 1.5 | 4561 |
| 3 | 15.88 | 488 | 3 | 6111 |
| MEAN | 15.48 | 423 | 2.17 | 4937 |
| SD | 0.35 | 61 | 0.76 | 1038 |

Pharmacokinetic data of the control formulations:

| NO | T1/2 H | CMAX ng/ml | TMAX H | AUC ng/ml * h |
|---|---|---|---|---|
| 1 | 13.57 | 313 | 2 | 3353 |
| 2 | 37.07 | 310 | 2 | 4112 |
| 3 | 15.89 | 293 | 1.5 | 4860 |
| MEAN | 22.18 | 305 | 1.83 | 4109 |
| SD | 12.95 | 11 | 0.28 | 753 |

As can be known from the data above, the present invention provides a method for preparing an efficient itraconazole formulation. The itraconazole formulation made by the method is superior to the commercially available SPORANOX capsule in terms of the data of the X-ray powder diffraction and SEM, the data of the in vitro dissolution test and the in vivo pharmacokinetic data in an animal. In addition, the present invention avoids the use of a surfactant, reducing side effects of the drug. The present invention provides an efficient, low toxic, and highly bioavailable efficient itraconazole formulation, and thus offers a more safe and effective option for patients and avoids a disadvantage of itraconazole having no effect in the body, which is a significant improvement in developing an itraconazole formulation.

BRIEF DESCRIPTION OF THE DRAWINGS

FIG. 3 is dissolution profiles of a commercially available SPORANOX capsule and an efficient formulation in a pH 1.0 solution; and FIG. 4 is drug-time curves of a commercially available SPORANOX capsule and an efficient formulation in a dog.

DETAILED DESCRIPTION OF THE PRESENT INVENTION

Figure 1:
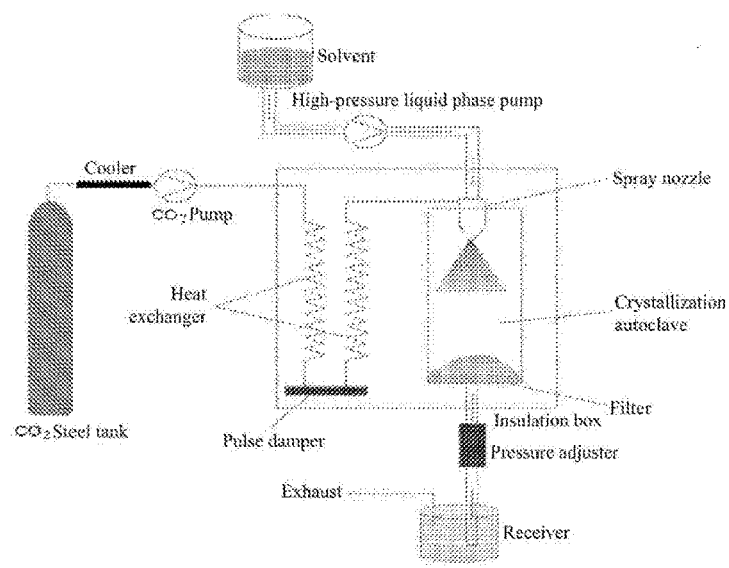
FIG. 1 is a schematic diagram of a supercritical fluid crystallization equipment.
Figure 2A:
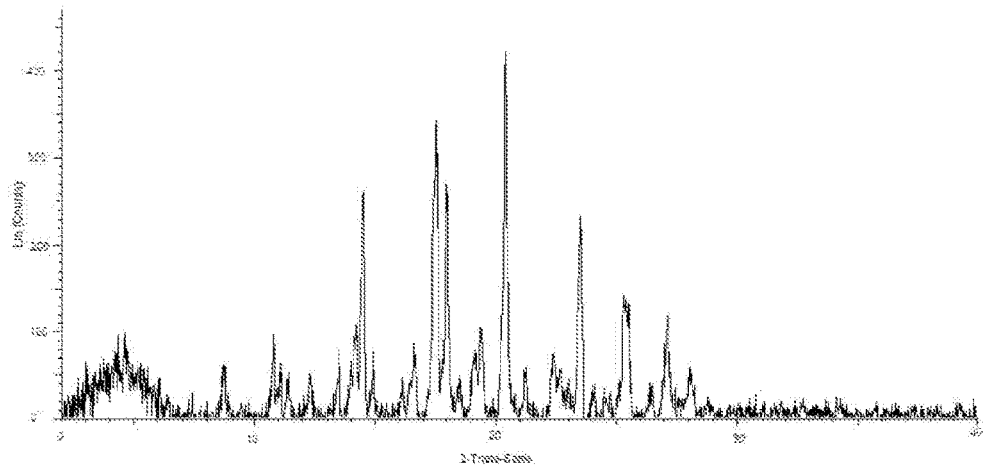
FIG. 2 is X-ray powder diffraction and SEM spectra of a drug substance and efficient formulation of itraconazole.
Figure 2B:
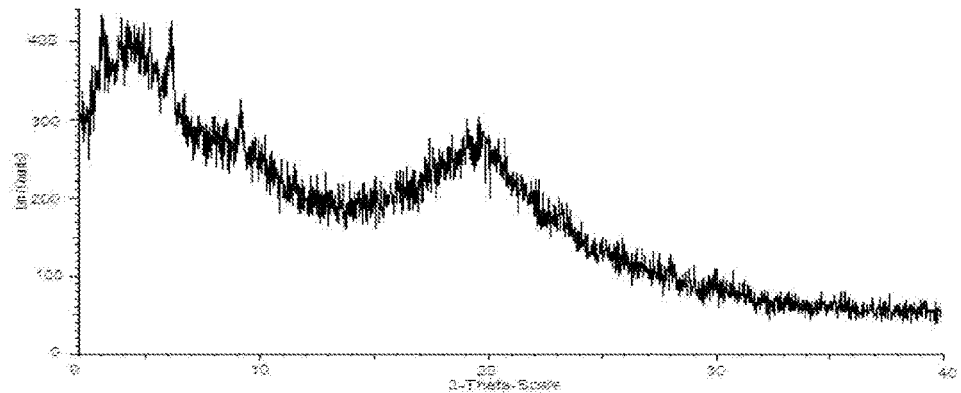

The following examples are only for further explanation or understanding of the content of the invention, and not intended to limit the scope of the invention.

Embodiment 1

| Ingredient | Percentage (%) |
|---|---|
| itraconazole | 35 |
| L-ascorbic acid | 15 |
| hydroxypropyl methylcellulose | 40 |
| pluronic F-127 | 10 |

(1) A mixture of itraconazole (0.63 g) and L-ascorbic acid (0.27 g) was added with 12 ml (1/1, v/v) a mixed solvent of methanol and dichloromethane and was dissolved by sonication, and hydroxypropyl methylcellulose (0.72 g) and pluronic F-127 (0.18 g) and then 48 ml dichloromethane were added and completely dissolved;

(2) carbon dioxide in a steel tank was fed, through a pressure regulating valve, into a crystallization autoclave in a supercritical fluid crystallization equipment system, where a flow rate of carbon dioxide was 10 ml/min, and a pressure was 50 Bar;

(3) the solution above was sprayed into the crystallization autoclave via a spray nozzle of the supercritical fluid crystallization equipment system, and the composite particles were separated out from the solution and collected at the bottom of the crystallization autoclave, where a flow rate of the solution was 0.1 ml/min; and (4) the resulting composite particles were encapsulated (formulation specifications: 50 mg/capsule and 100 mg/capsule).

Embodiment 2

| Ingredient | Percentage (%) |
|---|---|
| itraconazole | 40 |
| L-ascorbic acid | 10 |
| hydroxypropyl methylcellulose | 40 |
| pluronic F-127 | 10 |

(1) A mixture of itraconazole (0.72 g) and L-ascorbic acid (0.18 g) was added with 12 ml (1/1, v/v) a mixed solvent of methanol and dichloromethane and was dissolved by sonication, and hydroxypropyl methylcellulose (0.72 g) and pluronic F-127 (0.18 g) and then 12 ml dichloromethane were added and completely dissolved;

(2) carbon dioxide in a steel tank was fed, through a pressure regulating valve, into a crystallization autoclave in a supercritical fluid crystallization equipment system, where a flow rate of carbon dioxide was 20 ml/min, and a pressure was 95 Bar;

(3) the solution above was sprayed into the crystallization autoclave via a spray nozzle of the supercritical fluid crystallization equipment system, and the composite particles were separated out from the solution and collected at the bottom of the crystallization autoclave, where a flow rate of the solution was 0.4 ml/min; and (4) the resulting composite particles were encapsulated (formulation specifications: 50 mg/capsule and 100 mg/capsule).

Embodiment 3

| Ingredient | Percentage (%) |
| --- | --- |
| itraconazole | 55 |
| L-ascorbic acid | 10 |
| hydroxypropyl methylcellulose | 30 |
| pluronic F-127 | 5 |

(1) A mixture of itraconazole (0.99 g) and L-ascorbic acid (0.18 g) was added with 24 ml (1/1, v/v) a mixed solvent of methanol and dichloromethane and was dissolved by sonication, and hydroxypropyl methylcellulose (0.54 g) and pluronic F-127 (0.09 g) and then 12 ml dichloromethane were added and completely dissolved;

(2) carbon dioxide in a steel tank was fed, through a pressure regulating valve, into a crystallization autoclave in a supercritical fluid crystallization equipment system, where a flow rate of carbon dioxide was 30 ml/min, and a pressure was 100 Bar;

(3) the solution above was sprayed into the crystallization autoclave via a spray nozzle of the supercritical fluid crystallization equipment system, and the composite particles were separated out from the solution and collected at the bottom of the crystallization autoclave, where a flow rate of the solution was 1 ml/min; and (4) the resulting composite particles were encapsulated (formulation specifications: 50 mg/capsule and 100 mg/capsule).

Embodiment 4

| Ingredient | Percentage (%) |
| --- | --- |
| itraconazole | 30 |
| L-ascorbic acid | 15 |
| hydroxypropyl methylcellulose | 50 |
| pluronic F-127 | 5 |

(1) A mixture of itraconazole (0.54 g) and L-ascorbic acid (0.27 g) was added with 36 ml (2/1, v/v) a mixed solvent of methanol and dichloromethane and was dissolved by sonication, and hydroxypropyl methylcellulose (0.9 g) and pluronic F-127 (0.09 g) and then 12 ml dichloromethane were added and completely dissolved;

(2) carbon dioxide in a steel tank was fed, through a pressure regulating valve, into a crystallization autoclave in a supercritical fluid crystallization equipment system, where a flow rate of carbon dioxide was 50 ml/min, and a pressure was 130 Bar;

(3) the solution above was sprayed into the crystallization autoclave via a spray nozzle of the supercritical fluid crystallization equipment system, and the composite particles were separated out from the solution and collected at the bottom of the crystallization autoclave, where a flow rate of the solution was 3 ml/min; and (4) the resulting composite particles were encapsulated (formulation specifications: 50 mg/capsule and 100 mg/capsule).

What is claimed is:

1. A method for preparing an itraconazole formulation, comprising the following four steps:
   1) preparing a mixed solution: adding a mixed solvent of methanol and dichloromethane into a mixture of itraconazole and L-ascorbic acid, dissolving the mixture of itraconazole and L-ascorbic acid thereof, adding a hydroxypropyl methylcellulose and a poly(ethylene glycol)-block-poly(propylene glycol)-block-poly(ethylene glycol), wherein each of the poly(ethylene glycol) blocks has about 101 ethylene glycol repeating units and the poly(propylene glycol) has about 56 propylene glycol repeating units, and then dichloromethane into the mixed solvent, dissolving completely;
   2) feeding carbon dioxide: feeding carbon dioxide from a steel tank into a crystallization autoclave in a supercritical fluid crystallization equipment system through a pressure regulating valve;
   3) separating out a composite particle comprising an active drug and a polymer material: spraying the solution obtained in step (1) into the crystallization autoclave via a spray nozzle of the supercritical fluid crystallization equipment system, separating out the composite particles from the solution and collecting the composite particles at a bottom of the crystallization autoclave; and
   4) encapsulating the composite particles obtained.

2. The method for preparing according to claim 1, wherein the weight percentage of the itraconazole in the encapsulated composite particle is 30%-55%.

3. The method for preparing according to claim 1, wherein in the step (1), a volume ratio of the methanol to the dichloromethane is 1:1-1:9.

4. The method for preparing according to claim 1, wherein in the step (2), a flow rate of the carbon dioxide is 10-50 ml/min.

5. The method for preparing according to claim 1, wherein in the step (2), the carbon dioxide has a pressure of 50-130 Bar.

6. The method for preparing according to claim 1, wherein in the step (3), the spraying has a flow rate of 0.1-3 ml/min.

* * * * *